US00PP25985P2

(12) United States Plant Patent
van den Dool

(10) Patent No.: US PP25,985 P2
(45) Date of Patent: Oct. 13, 2015

(54) ***NANDINA* PLANT NAMED 'SUNSET IN PARADISE'**

(50) Latin Name: *Nandina domestica*
Varietal Denomination: Sunset in Paradise

(71) Applicant: Pieter van den Dool, Waddinxveen (NL)

(72) Inventor: Pieter van den Dool, Waddinxveen (NL)

( * ) Notice: Subject to any disclaimer, the term of this patent is extended or adjusted under 35 U.S.C. 154(b) by 47 days.

(21) Appl. No.: 13/999,873

(22) Filed: Mar. 31, 2014

(51) Int. Cl.
*A01H 5/00* (2006.01)

(52) U.S. Cl.
USPC ..... Plt./235

(58) Field of Classification Search
USPC ..... Plt./235
CPC ..... A01H 5/02; A01H 5/00
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

A new *Nandina domestica* plant particularly distinguished by having narrow leaves with fine texture, immature leaves having a deep burgundy color, and a compact growth habit, is disclosed.

3 Drawing Sheets

Genus and species: *Nandina domestica.*
Variety denomination: 'Sunset in Paradise'.

BACKGROUND OF THE NEW PLANT

The present invention comprises a new and distinct variety of *Nandina*, botanically known as *Nandina domestica* and hereinafter referred to by the variety name 'Sunset in Paradise'. 'Sunset in Paradise' was discovered as a naturally occurring whole plant mutation in a planting of an un-named *Nandina domestica* plant (unpatented) in June 2010 in Waddinxveen, The Netherlands.

In February 2011, 'Sunset in Paradise' was first asexually propagated by cuttings and tissue culture in Waddinxveen, The Netherlands. 'Sunset in Paradise' was found to reproduce true to type in successive generations of asexual propagation via cuttings and tissue culture in Waddinxveen, The Netherlands.

CROSS-REFERENCE TO RELATED APPLICATIONS

European Community Plant Variety Rights have been applied for on Feb. 12, 2013, Application Number 2013/0109. 'Sunset in Paradise' has not been made publicly available or sold more than one year prior to the filing date of this application.

SUMMARY

The following are the most outstanding and distinguishing characteristics of this new variety when grown under normal horticultural practices in Waddinxveen, The Netherlands.

1. Narrow leaves with fine texture;
2. Immature leaves having a deep burgundy color; and
3. A compact growth habit.

DESCRIPTION OF THE PHOTOGRAPHS

This new *Nandina* plant is illustrated by the accompanying photographs which show a whole plant view and close-up views of the foliage and stems. The photographs are of a plant approximately two-years-old grown in a greenhouse in Waddinxveen, The Netherlands in September 2013. The colors shown are as true as can be reasonably obtained by conventional photographic procedures.

DESCRIPTION OF THE NEW VARIETY

Figure 1:
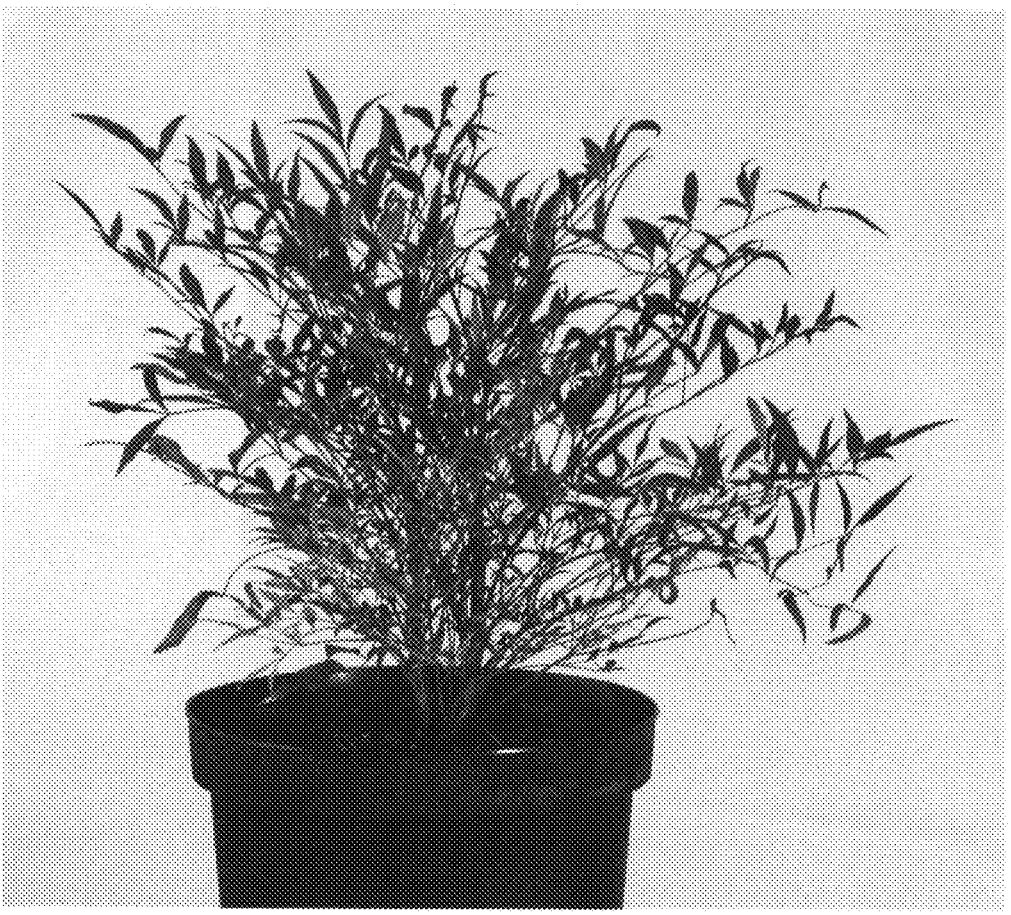
FIG. 1 shows an overall view of the whole plant in a container.
Figure 2:
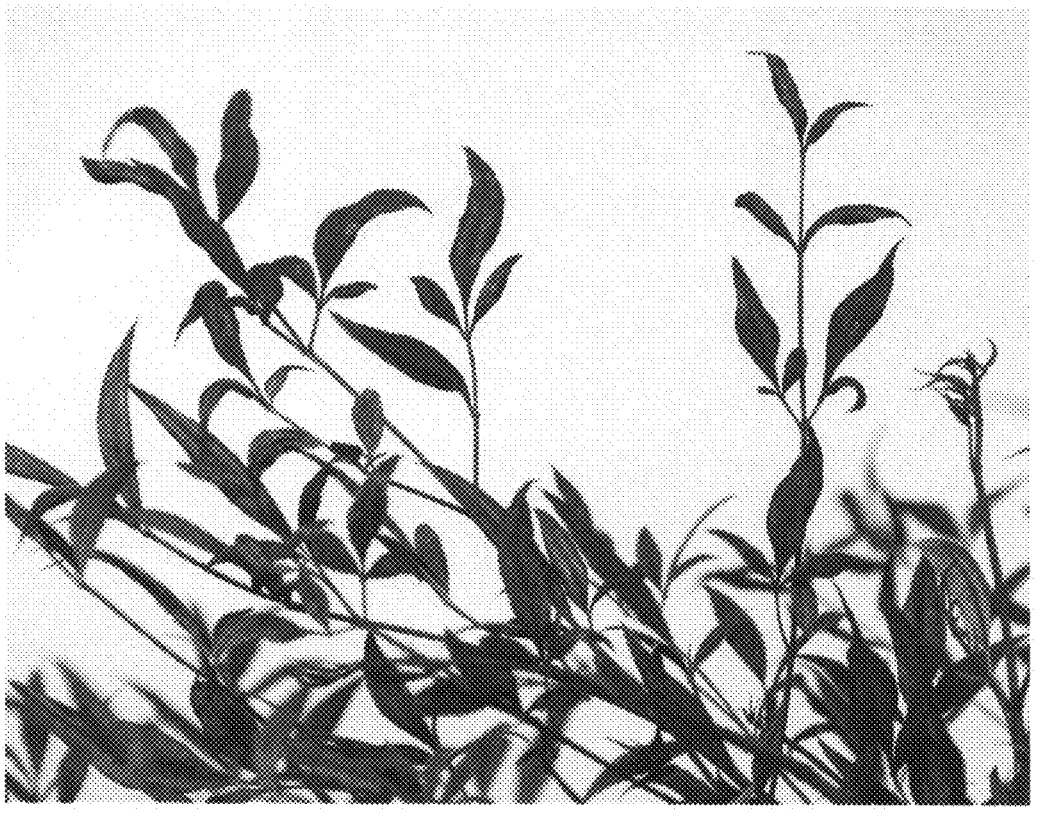
FIG. 2 shows a close-up of the immature foliage of the plant.
Figure 3:
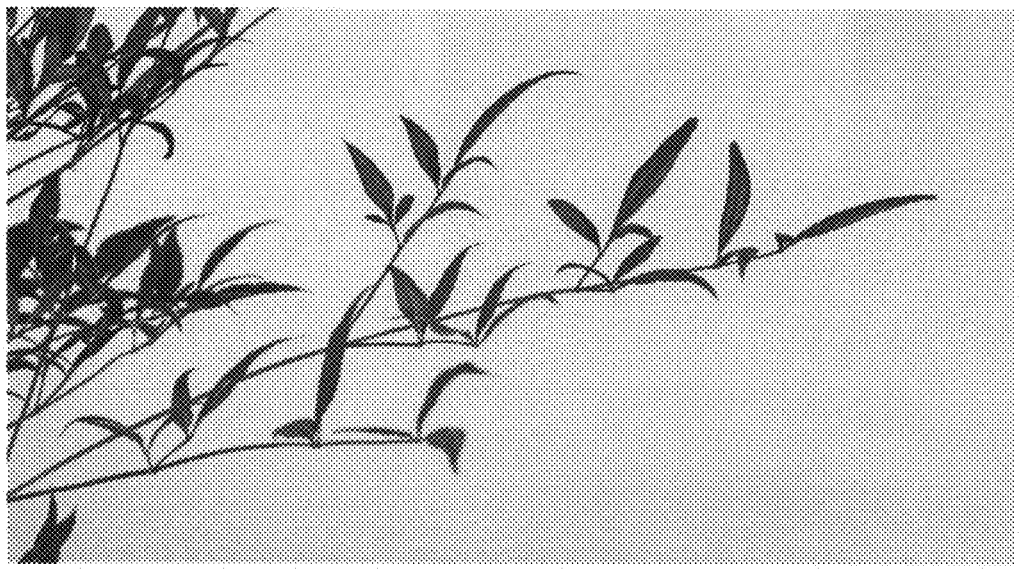
FIG. 3 shows a close-up of the mature foliage of the plant.

The following detailed descriptions set forth the distinctive characteristics of 'Sunset in Paradise'. The data which define these characteristics were collected from asexual reproductions carried out in Waddinxveen, The Netherlands. Data was collected on one-year-old plants grown in a greenhouse in Waddinxveen, The Netherlands in September 2013 where the average day temperatures were approximately 18° C. to 32° C. and where the average night temperatures were approximately 6° C. to 20° C. Color references are to The R.H.S. Colour Chart of The Royal Horticultural Society of London (R.H.S.), $5^{th}$ edition (2007).

Classification:
- *Family.*—Berberidaceae.
- *Species.*—*Nandina domestica.*
- *Variety.*—'Sunset in Paradise'.

Plant:
- *Type.*—Perennial, evergreen shrub.
- *Growth rate.*—Approximately 8.0 cm per season.
- *Plant vigor.*—Low to moderate.
- *Plant shape.*—Globular.
- *Growth habit.*—Broad upright.
- *Plant height.*—Approximately 28.0 cm.
- *Plant spread.*—Approximately 43.2 cm.
- *Time to produce a mature plant.*—Approximately two years from propagation.
- *Appropriate container systems.*—1.5 liter and larger containers.

*Hardiness.*—USDA zones 6b to 10.

*High temperature tolerance.*—At least tolerant up to 35° C.

*Low temperature tolerance.*—At least hardy to USDA zone 6b.

Stems:

*General.*—Not very free-branching; has on average 2 basal stems only; pinching may improve branching.

*Main stem.*—Length: Average is 13.7 cm. Diameter: Average is 0.3 cm.

*Lateral stem.*—Length: Average is 8.5 cm. Diameter: Average is 0.2 cm.

*Internode length.*—Average is 1.3 cm but ranges from 0.4 cm to 2.5 cm.

*Appearance.*—Rounded, slightly glossy.

*Aspect.*—Nearly vertical.

*Strength.*—Very strong.

*Color.*—RHS 152B to RHS 152C (Yellow-green); older stems and bark are RHS 200A (Brown).

*Texture.*—Glabrous; pubescence absent.

Leaves:

*Arrangement.*—Alternate, compound, and tripinnate; composed of an average of 92 leaflets per lateral leaf or ranging from between 58 and 119 leaflets.

*Quantity.*—Average is 11 per lateral branch.

*Shape.*—Broad rhomboidal.

*Length* (*excluding peduncle*).—Average is 24.5 cm.

*Width.*—Average is 20.2 cm.

*Pubescence.*—Absent.

*Rachis* (*main petiole*).—Length: Average is 20.8 cm. Diameter: Average is 0.15 cm. Color: Between RHS N137A (green) and RHS 139A (green).

*Durability of foliage to stresses.*—High.

*Leaflets.*—Quantity per leaf: Average of 92 leaflets per lateral leaf or ranging from between 58 and 119 leaflets. Shape: Narrow ovate to lanceolate. Apex: Long acuminate. Base: Long acuminate. Margin: Entire. Pubescence: Absent. Length: Average is 2.3 cm. Length of top leaflet: Average is 3.8 cm. Width: Average is 0.6 cm. Width of top leaflet: Average is 0.7 cm. Texture and appearance: Both upper and lower surfaces are glabrous; upper surface is moderately glossy, while lower surface is matte. Color, immature: Upper surface: Between RHS N186B (Greyed-purple) and RHS N186C (Greyed-purple). Lower surface: RHS 187B (Greyed-purple) to RHS 187C (Greyed-purple). Color, mature: Upper surface: Between RHS N137A (Green) and RHS 139A (Green). Lower surface: RHS 137C (Green). Venation pattern: Pinnate. Venation color: Upper surface: Between RHS N137A (Green) and RHS 139A (Green). Lower surface: RHS 144A (Yellow-green). Petiole length: Average is 3.4 cm. Petiole diameter: Average is 0.08 cm. Petiole color: RHS 143A (Green).

Flowers: None observed.

Reproductive organs: None observed.

Fruit and seed set: None observed.

Disease and pest resistance: Similar to other *Nandina domestica* varieties.

COMPARISON WITH PARENTAL LINES AND KNOWN VARIETIES

'Sunset in Paradise' is distinguished from its parent, an un-named typical *Nandina domestica,* as described in Table 1.

TABLE 1

Comparison with Parental line

| Characteristic | 'Sunset in Paradise' | Un-named Parent |
|---|---|---|
| Immature foliage color | Deep burgundy | Green |
| Mature foliage color | Dark green than parent | Lighter green than 'Sunset in Paradise' |
| Foliage structure | Significantly finer foliage structure than parent | |
| Growth habit | Significantly more compact than parent | Significantly less compact than 'Sunset in Paradise' |

'Sunset in Paradise' can be compared to the commercial *Nandina* plant varieties 'Sunset' (U.S. Plant Pat. No. 24,748, filing date Jul. 27, 2012) and 'Firepower' (Unpatented). Differences between the two varieties are described in Table 2.

TABLE 2

Comparison with known varieties

| Characteristic | 'Sunset in Paradise' | 'Sunset' | 'Firepower' |
|---|---|---|---|
| Foliage structure | Less coarse foliage structure than 'Sunset' | Coarser foliage structure than 'Sunset in Paradise' | |
| Growth habit | More compact than 'Sunset' | Less compact than 'Sunset in Paradise' | |
| Leaflets and leaf width | Significantly narrower than 'Firepower' | | Significantly wider than 'Sunset in Paradise' |
| Immature foliage color | Deep burgundy | | Orange |

I claim:

1. A new and distinct variety of *Nandina* plant named 'Sunset in Paradise' as illustrated and described herein.

* * * * *